United States Patent
Masuda

[11] Patent Number: 5,259,830
[45] Date of Patent: Nov. 9, 1993

[54] AID FOR INDUCING SLEEP OR THE LIKE UTILIZING LIGHT

[75] Inventor: Isamu Masuda, Fukuoka, Japan

[73] Assignee: Nihonkenkozoshinkenkyukai Co., Ltd., Fukuoka, Japan

[21] Appl. No.: 836,342

[22] PCT Filed: Jul. 29, 1991

[86] PCT No.: PCT/JP91/01014
§ 371 Date: Feb. 26, 1992
§ 102(e) Date: Feb. 26, 1992

[87] PCT Pub. No.: WO92/03177
PCT Pub. Date: Mar. 5, 1992

[30] Foreign Application Priority Data

Aug. 11, 1990 [JP] Japan .................. 2-213123

[51] Int. Cl.⁵ .................. A61M 21/00
[52] U.S. Cl. .................. 600/27
[58] Field of Search .................. 600/26-28

[56] References Cited

U.S. PATENT DOCUMENTS 4,858,609  8/1989  Cole .................. 600/26
5,149,317  9/1992  Robinson .................. 600/27

FOREIGN PATENT DOCUMENTS 277053  6/1990  Spain .

Primary Examiner—Kyle L. Howell
Assistant Examiner—J. P. Lacyk
Attorney, Agent, or Firm—Jordan and Hamburg

[57] ABSTRACT

An aid for inducing sleep has a total of four light sources positioned in front of each eye of the user. The light sources are symmetrically arranged with respect to the centers of the eyes of the user, with two light sources at each eye being horizontally aligned and the other two light sources at each eye being vertically aligned.

6 Claims, 5 Drawing Sheets

AID FOR INDUCING SLEEP OR THE LIKE UTILIZING LIGHT

FIELD OF THE INVENTION

This present invention relates to an aid for inducing sleep or the like which induces a person to a state such as sleep or mediation utilizing light.

BACKGROUND OF THE INVENTION

As the conventional inducing aid of this kind, there is an aid having a configuration wherein a light emitting body is disposed at each of the both-side positions of a bandage. When this bandage is attached to the face, the eyes are closed, and thereafter each light emitting body performs a blinding operation at a predetermined period, light from each light emitting body is projected intermittently from above the eyelid. When this light stimulation acts on the brain through the optic nerve, the brain waves transit from $\alpha$ waves $\beta$ waves, and induces the person to a sleeping state or the like.

However, the inducing aid of this kind has a problem that the interval between the right and left eyes individually varies more or less when the bandage is attached, and therefore the right and left light emitting bodies deviate often from the positions of both eyes, and the effect thereof is reduced by half. The present invention purposes to reliably obtain a desired inducing effect even if individual differences exists in the interval between both eyes.

SUMMARY OF THE INVENTION

An aid for inducing sleep or the like utilizing light of the present invention is provided with a bandage large enough to cover both eyes, and a holder for holding the bandage at the position of the eyes, and is configured by disposing a light emitting body at each of the two sides and top and bottom positions of the positions of each eye around the center thereof.

In accordance with the present invention, a light emitting body is disposed at each of the both of the sides and top and bottom positions of the positions of both eyes of the bandage around the centers thereof, and therefore when the bandage is attached, any of the light emitting bodies of the both-side positions or the top and bottom positions corresponds to each of the positions of both of the eyes even if the interval between the right and left eyes individually varies more or less, and therefore a desired inducing effect is obtained reliably.

DESCRIPTION OF THE PREFERRED EMBODIMENT

Figure 1:
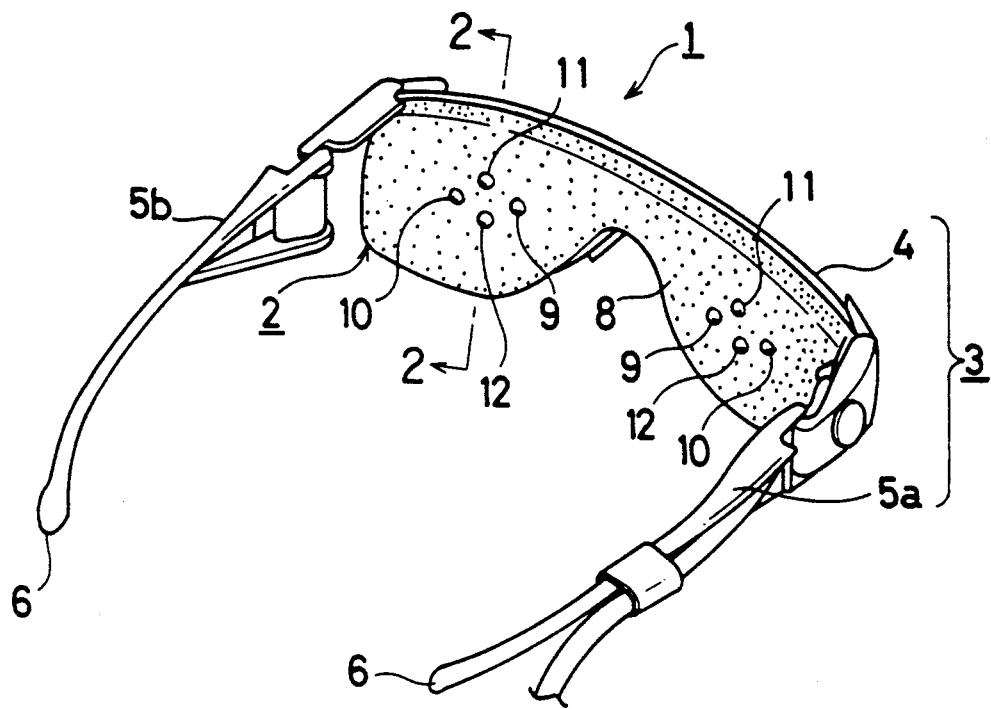
FIG. 1 is a perspective view of an inducing aid of an embodiment in accordance with the present invention.
Figure 2:
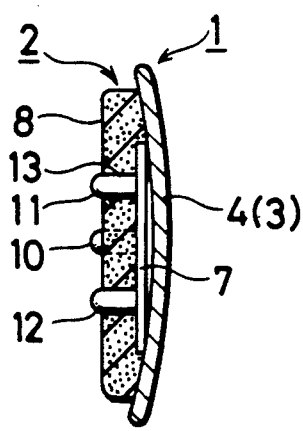
FIG. 2 is a cross-sectional view taken along a line 2—2 in FIG. 1.

FIG. 1 and FIG. 2 show an aid for inducing sleep or the like 1 of an embodiment in accordance with the present invention. This inducing aid 1 has a whole form similar to eyeglasses, and is configured with a bandage 2 and a holder 3.

The holder 3 comprises a main body 4 consisting of color glasses and a pair of left and right supports 5a and 5b pivotally connected to opposite ends of the main body 4 in a freely bendable manner. Each of the supports 5a and 5b are curved along the side-shape of the face, and fixing parts 6 to the ears are formed at the tips thereof.

The above-mentioned bandage 2 is configured with a pair of right and left printed boards 7 and 7 mounted on the main body 4 of the holder 3, and an eye-touch plate 8 superposed continuously on the both boards 7, and light emitting bodies 9–12 consisting of right and left groups of four light emitting diodes each mounted on the both boards 7.

The above-mentioned eye-touch plate 8 is formed with a soft foaming agent in a shape running along the main body 4 of the holder 3, and four though-holes 13 are opened at the positions of both eyes, and the above-mentioned light emitting bodies 9–12 are projected through the respective through-holes 13.

Figure 3:
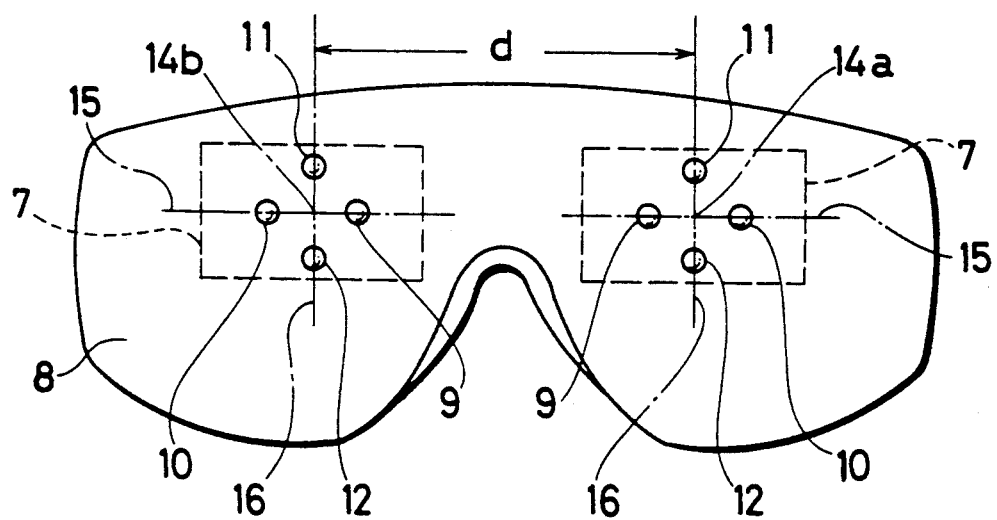
FIG. 3 is a front view of a bandage.

As shown in FIG. 3, these light emitting bodies 9–12 are disposed at both sides and the top and bottom positions of the positions of both eyes around the centers 14a and 14b thereof. The above-mentioned centers 14a and 14b are set statistically from an average distance d between the both eyes, and the light emitting bodies 9 and 10 are positioned at the positions on a horizontal line 15 symmetrically with respect to the center 14a and 14b, and the light emitting bodies 11 and 12 are positioned at the positions on a vertical line 16 symmetrically with respect to the centers 14a or 14b, respectively. In the case of this embodiment, the distance between the light emitting bodies 9 and 10 at the positions of both sides is set to 12.5 mm, and the distance between the top and bottom light emitting bodies 11 and 12 is set to 13.5 mm, respectively.

Among these light emitting bodies 9–12, for the light emitting bodies 9 and 10 at the inside position and the top side position, light emitting diodes emitting red light are used, and for the light emitting bodies 10 and 12 at the outside position and the bottom side position, light emitting diodes emitting green light are used.

Figure 4:
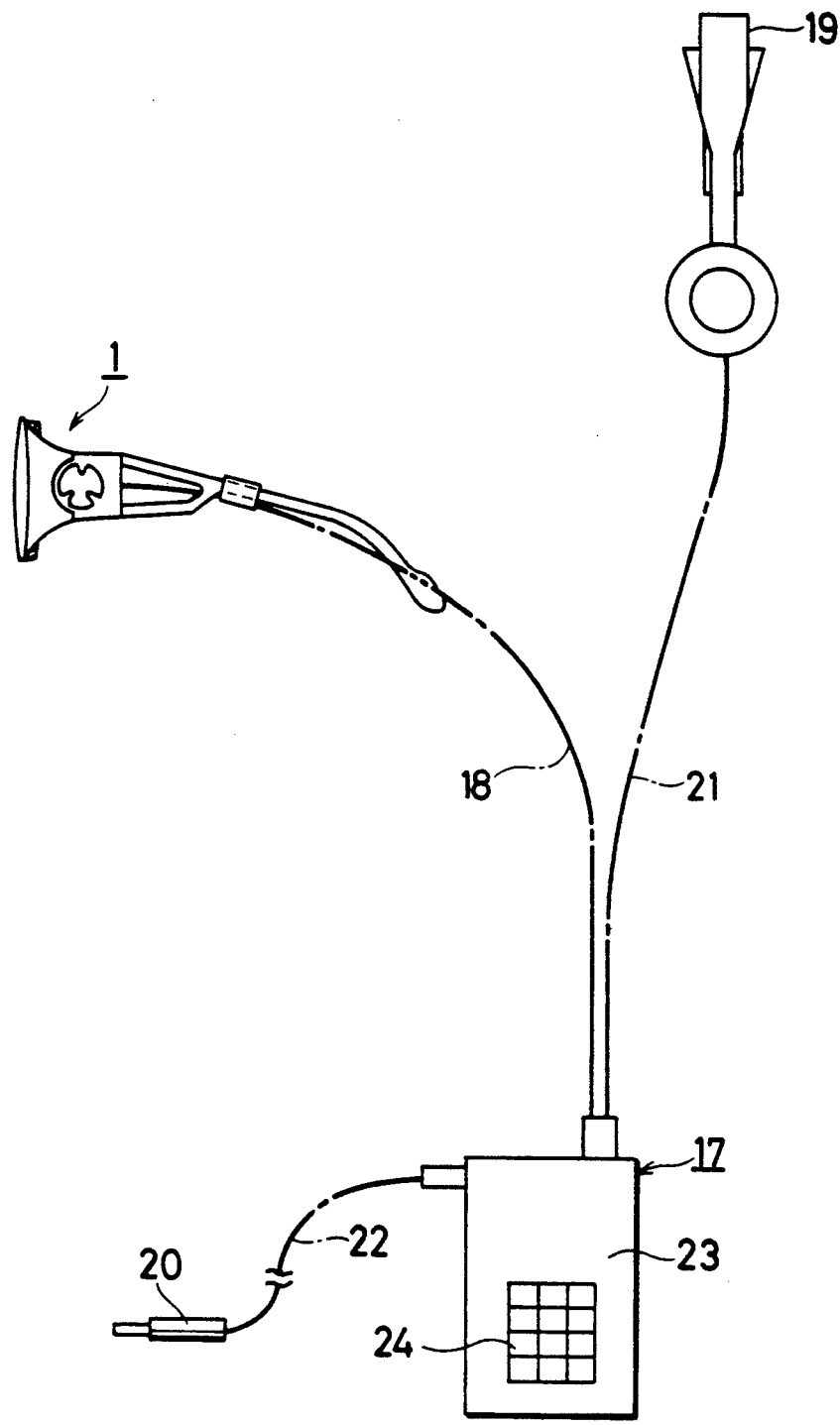
FIG. 4 is a front view showing a state of connection of the inducing aid to a drive controlling apparatus.

As shown in FIG. 4, the above-mentioned inducing aid 1 is electrically connected to a drive controlling apparatus 17 by a connecting wire 18, and to this drive controlling apparatus 17, a headphones 19 and a power connecting terminal 20 are further, connected respectively by the connecting wires 21 and 22.

The above-mentioned drive controlling apparatus 17 incorporates a controlling circuit in a case 23, and a keyboard 24 with plural keys is installed on the surface of the case 23.

Figure 6:
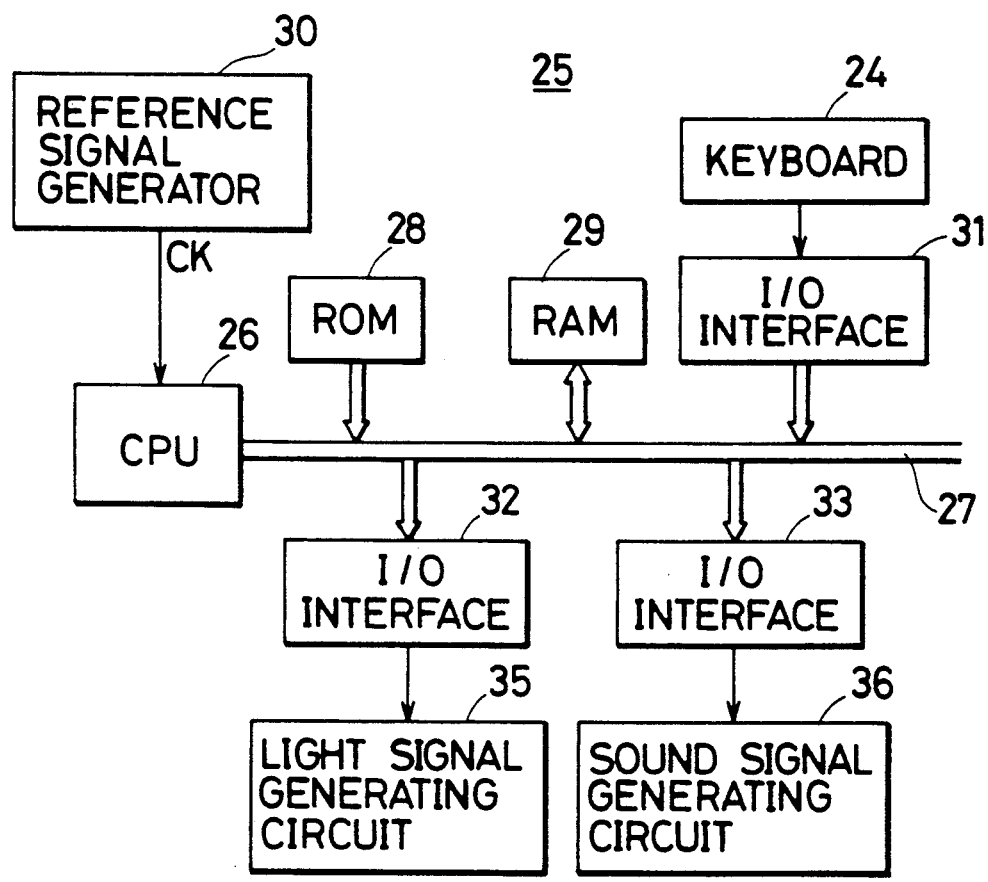
FIG. 6 is a block diagram of a controlling circuit.

FIG. 6 shows an example of circuit configuration of a controlling circuit 25. In FIG. 6, a CPU 26 is a main unit of arithmetic operations and controls, being connected to a ROM 28 storing programs and a RAM 29 as a working area through a Bus 27. To the CPU 26, a reference signal generator 30 is connected, and a clock signal CK is supplied. To the above-mentioned Bus 27, the keyboard 24, a light signal generating circuit 35 and a sound signal generating circuit 36 and the like are connected through I/O interfaces 31–33.

The light signal generating circuit 35 drives the above-mentioned inducing aid 1, and the sound signal generating circuit 36 drives the headphones 19, and the light signal generating circuit 35 outputs light signals for making the red light emitting bodies 9 and 11 and the green light emitting bodies 10 and 12 alternately perform blinking operations to the inducing aid 1, and the sound signal generating circuit 36 outputs sound signals for intermittently generating buzzer sound to the headphones 19, respectively.

Time of lighting and period of blinking of the light emitting bodies 9-12, and frequency, time of generation and period of intermittence of buzzer sound are set by a plurality of programs stored in the ROM 28, and these programs can be selected by the operation of the keyboard 24. In the case of this embodiment, the period of blinking of the light emitting bodies 9-12 and the period of intermittence of buzzer, sound are made to agree with each other.

Figure 5:
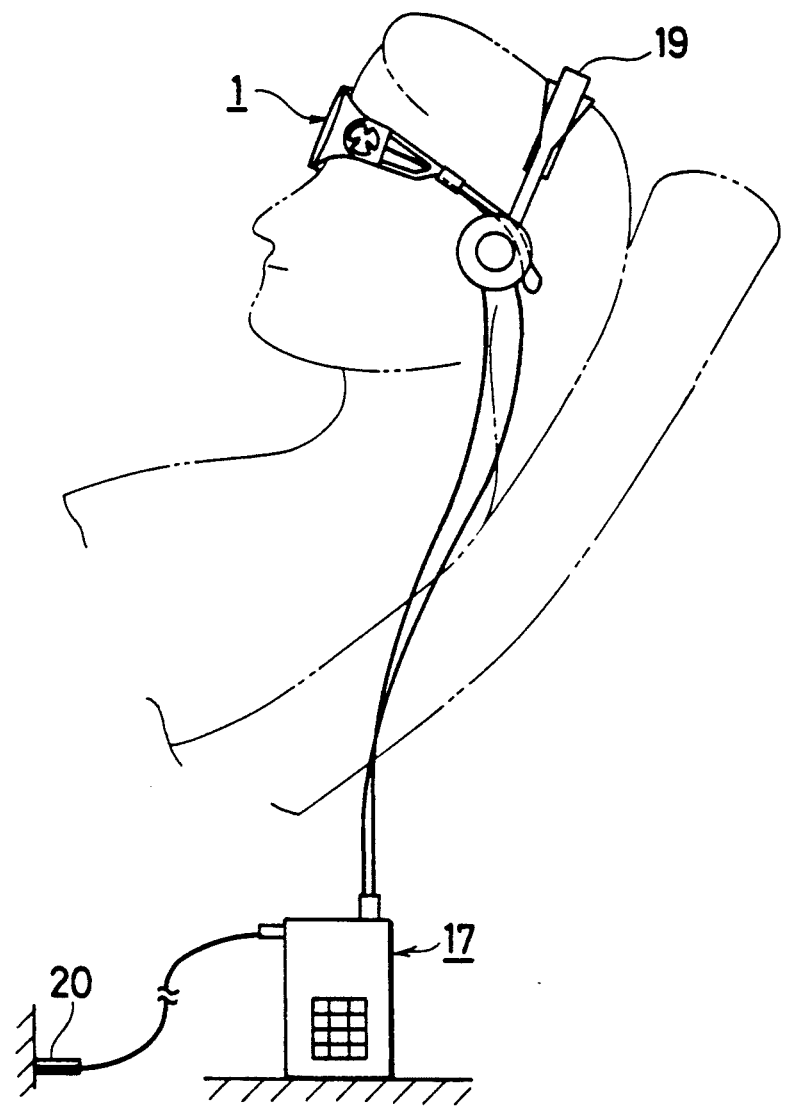
FIG. 5 is an explanatory view showing a state of use.

FIG. 5 shows a manner in which this inducing aid 1 is used. The inducing aid 1 is held at the position of eyes, and the headphones 19 is set at the ears, and then the drive controlling apparatus 17 is driven. In this case, when the bandage 2 is attached, any of the light emitting bodies 9 and 10 at the positions of both sides or the light emitting bodies 11 and 12 at the top and bottom positions corresponds to each of the positions of both eyes even if the interval between the right and left eyes individually varies more or less, and therefore a desired inducing effect is obtained reliably.

What is claimed is:

1. An aid for inducing sleep utilizing light, comprising a bandage large enough to cover both eyes of a user, holder means for holding said bandage at a position covering the eyes of the user, the bandage having left and right portions for covering the left and right eyes, respectively, of the user, a total of four light sources, including first, second, third and fourth light sources, positioned in each of said left and right portions of said bandage, to direct light to the respective eye of said user, with said first and second light sources being horizontally aligned in said left and right portions, symmetrically positioned with respect to a center position of the respective portion, and said third and fourth light sources being vertically aligned in each of said left and right portions and symmetrically positioned with respect to said center positions.

2. An aid for inducing sleep utilizing light in accordance with claim 1, wherein among said light sources, the light sources at inside and the top-side positions are light emitting diodes emitting red light, and the light sources at outside and the bottom-side positions are light emitting diodes emitting green light.

3. An aid for inducing sleep comprising a bandage having left and right portions, means for holding said bandage to cover the eyes of a user, with said left and right portions covering the left and right eyes of the user, and a total of four light sources positioned in each of said left and right portions of said bandage, a first two of said light sources in each of said portions being aligned in a first direction extending between said left and right portions symmetrical with respect to a center position of the respective portion, and the other two light sources in each portion being aligned with one another in a direction normal to said first direction and also positioned symmetrical with respect to the center position of the respective portion.

4. The aid of claim 3 wherein two of said light sources in each said portion emit red light, and two of said light sources in each portion emit green light.

5. An aid for inducing sleep comprising a bandage having left and right portions, means for holding said bandage to cover the eyes of a user, with said left and right portions covering the left and right eyes of the user, each of said bandage portions having right, left, top and bottom sides and a center position, and a total of four light sources positioned in each of said left and right portions of said bandage, a first two of said light sources being aligned horizontally between said left and right sides of the respective bandage portion symmetrically with respect to the respective center position, and the other two light sources in each portion being aligned vertically between the top and bottom sides of said portions and normal to said first direction and symmetrically with respect to the respective center position.

6. The aid of claim 5 wherein the light sources in each said portion toward the other respective portion, and the light sources toward said top side, emit red light, and said other light sources in each portion emit green light.

* * * * *